US012360393B2

(12) United States Patent
Cowart

(10) Patent No.: US 12,360,393 B2
(45) Date of Patent: Jul. 15, 2025

(54) EYE SHIELD FRAME WITH IMPROVED FIT

(71) Applicant: DeRoyal Industries, Inc., Powell, TN (US)

(72) Inventor: Walter C. Cowart, Blaine, TN (US)

(73) Assignee: DeRoyal Industries, Inc., Powell, TN (US)

( * ) Notice: Subject to any disclaimer, the term of this patent is extended or adjusted under 35 U.S.C. 154(b) by 650 days.

(21) Appl. No.: 17/592,591

(22) Filed: Feb. 4, 2022

(65) Prior Publication Data

US 2023/0251503 A1    Aug. 10, 2023

(51) Int. Cl.
*G02C 1/02*    (2006.01)

(52) U.S. Cl.
CPC ..................... *G02C 1/02* (2013.01)

(58) Field of Classification Search
CPC ........................................ G02C 1/02
USPC ........................................... 351/60
See application file for complete search history.

(56) References Cited

U.S. PATENT DOCUMENTS

| | | | | |
|---|---|---|---|---|
| 5,648,832 A * | 7/1997 | Houston | ............ | G02C 7/02 351/159.02 |
| 5,760,868 A * | 6/1998 | Jannard | ............ | A61F 9/02 351/41 |
| 5,841,506 A * | 11/1998 | Karasawa | ............ | G02C 9/00 351/49 |
| 6,758,562 B1 * | 7/2004 | Barnette | ............ | G02C 5/16 351/114 |
| 7,524,057 B2 * | 4/2009 | Agazarova | ............ | G02C 5/008 351/122 |
| 2015/0323807 A1 * | 11/2015 | Marini | ............ | G02C 5/146 351/114 |

FOREIGN PATENT DOCUMENTS

| | | |
|---|---|---|
| WO | 9117468 A1 | 11/1991 |
| WO | 9603061 A1 | 2/1996 |

OTHER PUBLICATIONS

Pinnacle Polymers, 1120 H, 21 Melt Flow Homoplymer Polypropylene with Nucleation and Antistat for Injection Molding; Garyville, LA, USA The date of this publication is not known, but it is requested that it be considered as prior art for purposes of examination.

Pinnacle Polymers, 2160H, 65 Melt Flow Impact Copolymer for Injection Molding, Garyville, LA, USA The date of this publication is not known, but it is requested that it be considered as prior art for purposes of examination.

(Continued)

*Primary Examiner* — Sharrief I Broome
(74) *Attorney, Agent, or Firm* — Luedeka Neely, P.C.

(57) ABSTRACT

An eyewear frame of improved comfort, including a one-piece non-folding eyewear frame to which a shield is attachable to provide eyewear, the frame being made of plastic having a flexural modulus of from about 250,000 psi to about 310,000 psi (ASTM D790A), with the frame having a brow piece and a pair of symmetric left and right ear pieces extending away from the brow piece at opposite ends of the brow piece, each ear piece terminating at a free end, with the free ends of the brow pieces being spaced apart from one another to define a gap, with the frame having a maximum width such that the ratio of the maximum width to the gap is above 3.

7 Claims, 5 Drawing Sheets

(56) References Cited

OTHER PUBLICATIONS

Joanna Richards, Formalities Officer, European Patent Office, Munich, Germany, Application 23 153 033.8-1020, Communication Pursuant to Article 94(3)EPC, EPO Form 2906 01.91TRI, dated Apr. 2, 2024.
Makeitfrom.com, Internet Archive, Way Back Machine, Cellulose Acetate (CA), Mechanical Properties, Sep. 17, 2021.
European Patent Office, Munich, Germany, European Search Report, Jun. 20, 2023, Application No. EP 23 15 3033 (9 pages).
Omnexus The material selection platform Plastics and Elastomers, Sep. 6, 2023, (12 pages).
European Patent Office, EPO Form 2906 01.91TRI, Communication pursuant to Article 94(3) EPC, (6 pages) Munich, Germany.

* cited by examiner

EYE SHIELD FRAME WITH IMPROVED FIT

FIELD

This disclosure relates to the field of frames for eyewear. More particularly, this disclosure relates to a polymeric frame for eyewear, such as eye shields, having improved fit.

BACKGROUND

Improvement is desired in the construction of eyewear frames, such as frames for eye shields, and particularly plastic frames for disposable eye shields.

Conventional plastic frames for eye shields typically fit poorly and feel loose on the head of many wearers and tend to not snugly engage the head of the wearer. If the wearer engages in any motion of their head the frame can jiggle and the lens or shield of the eye shield often ends up sliding down the bridge of the nose of the wearer.

Also, the plastic material from which the frame is made typically has a light bend pressure on the head of the wearer and does not firmly grip or engage the head of the wearer. This further adds to the problem of poor fit of the frames.

What is desired are plastic eye shield frames that have improved fit.

SUMMARY

The above and other needs are met by eyewear frames of improved fit.

In one aspect, an eyewear frame of improved comfort according to the disclosure includes a one-piece non-folding eyewear frame to which a shield is attachable to provide eyewear, the frame being made of plastic having a flexural modulus of from about 250,000 psi to about 310,000 psi (ASTM D790A).

The frame has a brow piece and a pair of symmetric left and right ear pieces extending away from the brow piece at opposite ends of the brow piece. Each ear piece terminates at a free end, with the free ends of the brow pieces being spaced apart from one another to define a gap, with the frame having a maximum width such that the ratio of the maximum width to the gap is above 3.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1A:
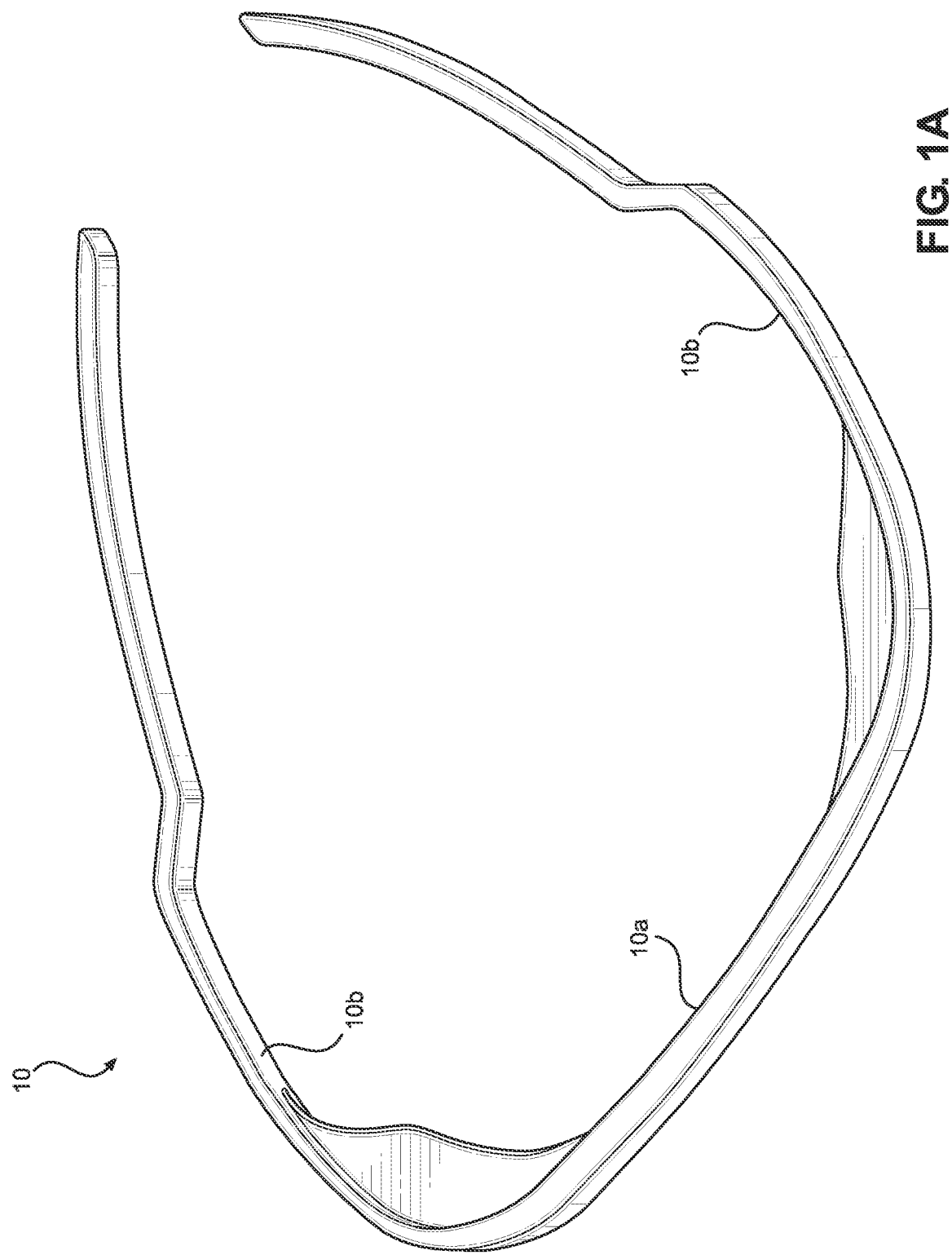
FIG. 1A is a perspective view of an eye shield frame according to the disclosure, and FIG. 1B includes the shield.
Figure 1B:
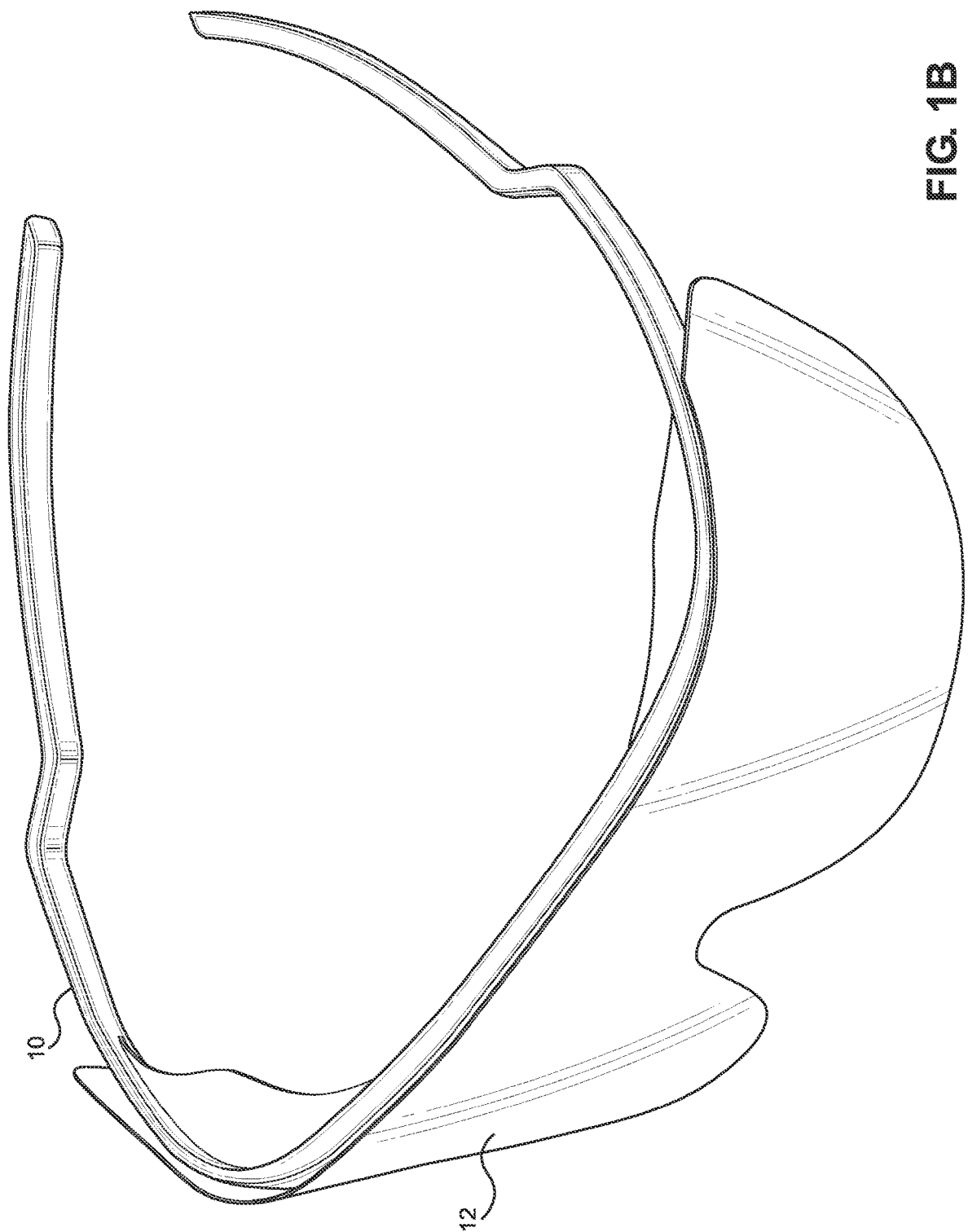
Figure 2:
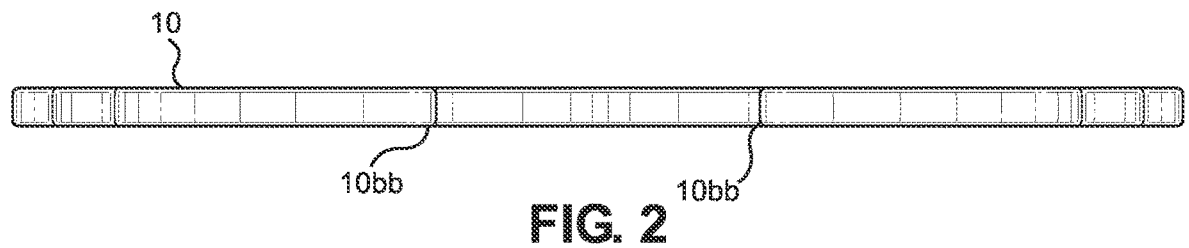
FIG. 2 is an end view of the frame.
Figure 3:
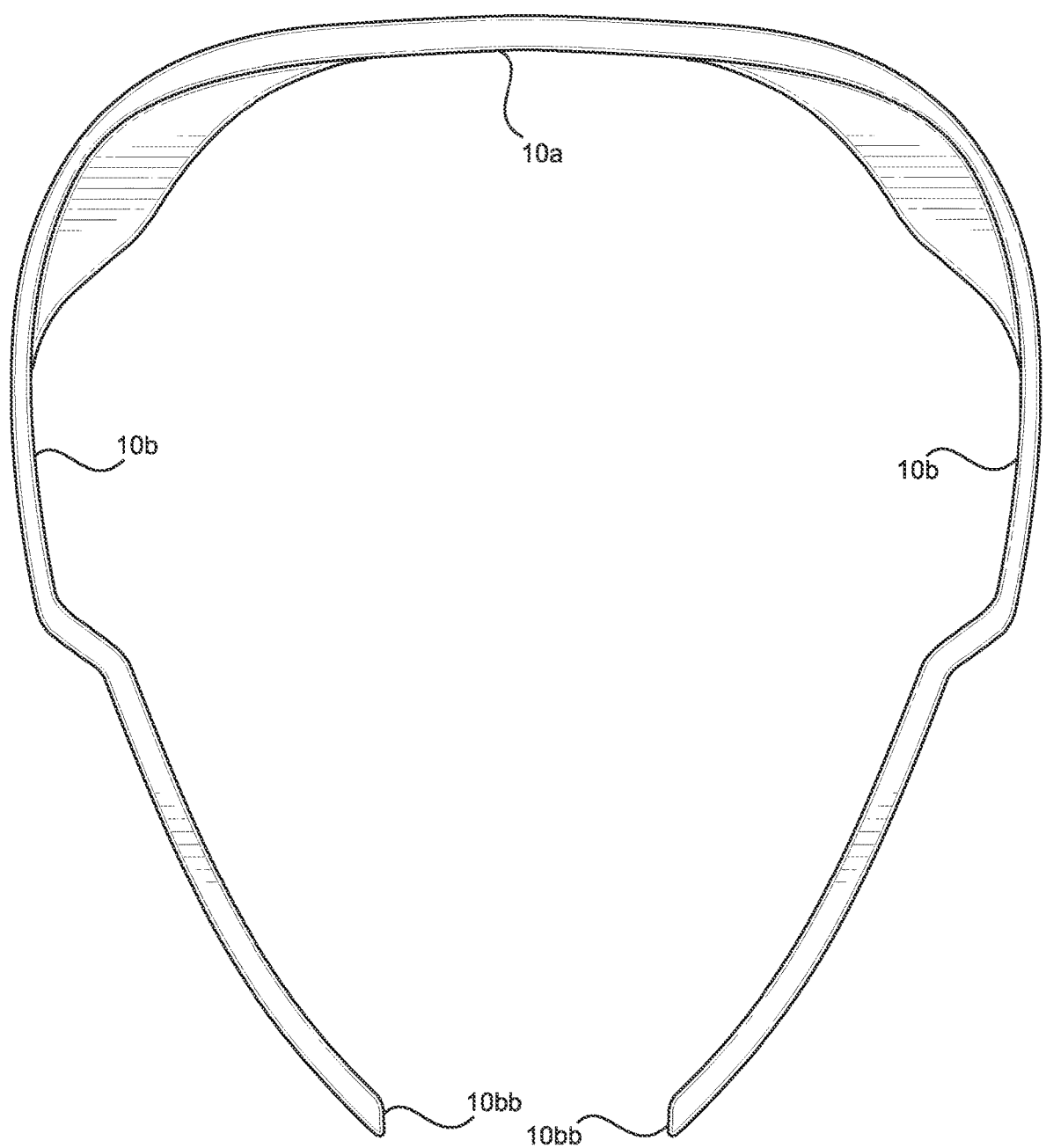
FIG. 3 is a top view of the frame.

With reference to the drawings, there is shown an eyewear frame in the form of an eye shield frame 10 according to the disclosure. The frame 10 supports a lens or shield 12 and is configured for use by an adult user.

The frame 10 as described herein has been observed to provide an improved fit for the majority of adult users as compared to conventional one-piece plastic frames. It has been discovered that the structure of the frame 10 as described herein in combination with the stiffer material described herein to make the frame 10 renders an eyewear frame having improved fit.

The frame 10 is a non-folding polymeric or plastic frame of one-piece injection molded construction and intended to be disposable. This type of frame is distinguishable from eyewear frames of the type having multiple assembled parts and ear or temple pieces connected by hinges.

The frame 10 includes a frontal brow piece 10a to which the shield 12 attaches and a pair of ear pieces 10b extending generally rearward and away from the brow piece 10a at opposite ends of the brow piece 10a. The ear pieces 10b are symmetric to one another, with one of the ear pieces 10b configured to be the left side of the frame 10 and the other of the ear pieces 10b configured to be the right side of the frame 10.

The frame 10 has a maximum width W, which coincides with the distance between bend points BP of the frame 10. The bend points BP represent the locations on the frame 10 where the ear pieces 10b bend when flexed and where the ear pieces 10b are begin to extend inwardly so as to lie inwardly of the maximum width of the frame 10. For the shown frame 10, the maximum width W is between about 5.6 inches and about 6.2 inches, most preferably about 5.9 inches.

In providing the frame 10 according to the disclosure, the free rear ends 10bb of the ear pieces 10b extend inwardly from the bend points BP and are spaced apart by a gap G of from about 1.4 inches to about 1.8 inches, most preferably about 1.6 inches. Thus, the frame 10 is configured so that the ratio of the maximum width W to the gap G ranges from about 3.1 to about 4.4, and most preferably about 3.7. Thus, frame 10 preferably has a gap G of less than 2.0 inches and a ratio of the maximum width to the gap above 3 and less than 5.

Figure 4:
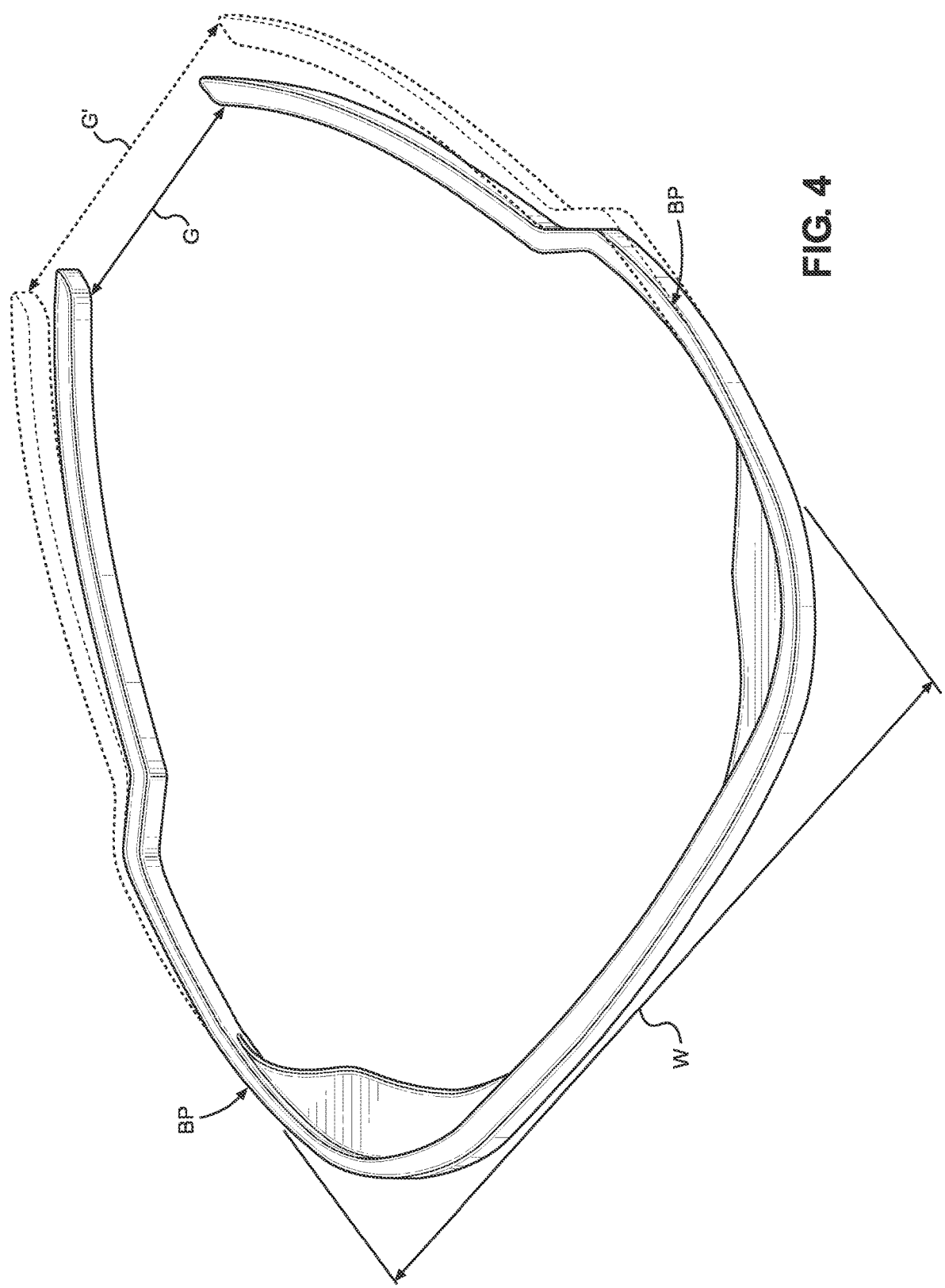
FIGS. 4 and 5 are perspective and top views of the frame showing the maximum width of the frame and the gap between free rear ends of the ear pieces according to the disclosure. In comparison a much wider gap between free rear ends of the ear pieces of a conventional frame is shown in dashed lines.
Figure 5:
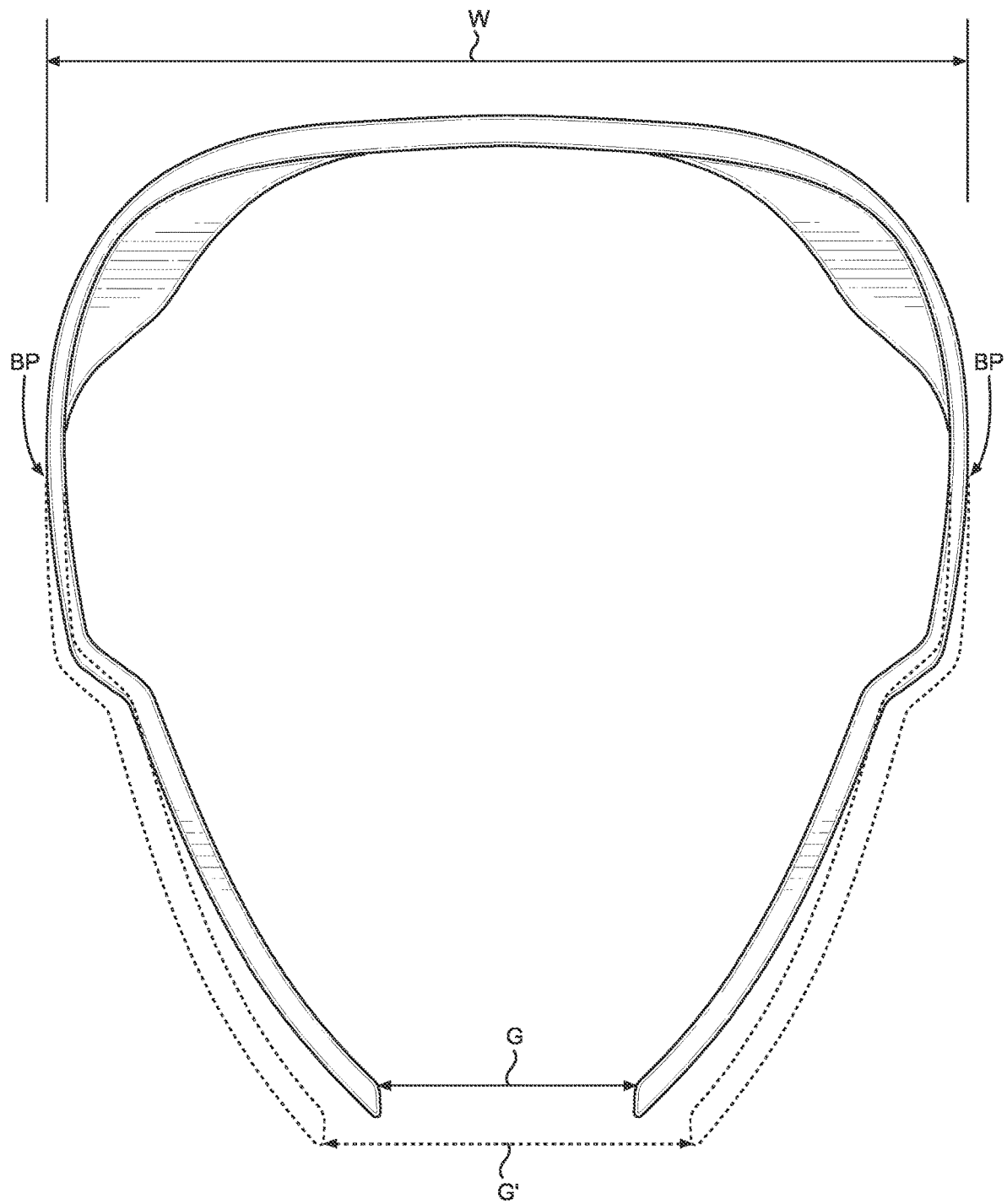

In comparison, a conventional frame corresponds in shape to the frame 10, except in one important difference, the ear pieces of a conventional frame (shown in dashed lines in FIGS. 4 and 5) define a significantly wider gap G' in the context of a frame for eyewear. As will be noted, the conventional frame has the same maximum width W, but the gap G' thereof is wider than the gap G according to the disclosure. The gap G' ranges from about 2.2 inches to about 2.6 inches, and generally about 2.4 inches. Thus, the conventional frame has a ratio of the maximum width W to the gap G' ranging from about 2.1 to about 2.8, and generally about 2.5. Thus, conventional frames have a gap above 2.0 inches and a ratio of the maximum width to the gap is less than 3.

In combination with the foregoing described dimensions of the frame 10 according to the disclosure, it has been discovered that the frame 10 as desirably configured above will provide a frame having an improved fit if made utilizing a significantly stiffer plastic than is conventionally used for eyewear frames of this type. Stiffness is a mechanical property of plastic, and the stiffness of a plastics is described by its flexural modulus (the ability of a material to bend). Flexural modulus is measured in pounds per square inch (psi). The higher the flexural modulus, the stiffer the material; the lower the flexural modulus, the more flexible it is. A standard test to determine flexural modulus is ASTM D790A—(1% secant) at 1.27 mm/min using an ASTM Type I specimen, 3.2 mm thick (injection molded per ASTM D4101-92a).

A conventional polymeric resin plastic used for making eyewear frames is a polypropylene resin having a flex mod of 190,000 psi and available under the name Pinnacle 2160H available from Pinnacle Polymers of Garyville, Louisiana (www.pinnaclepolymers.com). In accordance with the disclosure, this plastic has a flexural modulus determined by ASTM D790A of 190,000 psi.

In accordance with the disclosure, suitable plastics for use with the frame 10 have a much higher flexural modulus determined by ASTM D790A of from about 250,000 psi to about 310,000 psi, and most preferably about 280,000 psi. An example of a preferred plastic is Polypropylene 1120H available from Pinnacle Polymers of Garyville, Louisiana (www.pinnaclepolymers.com) having a flexural modulus of 280,000 psi (ASTM D790A).

It has been discovered frames having improved fit according to the disclosure may be achieved by the combination of a frame made of plastic having a flexural modulus of from about 250,000 psi to about 310,000 psi, and having a gap G between the ends 10bb of the ear pieces 10b of less than 2.0 inches and a ratio of the maximum width to the gap above 3.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An eyewear frame, comprising:
a one-piece non-folding eyewear frame to which a shield is attachable to provide eyewear, the frame being made of plastic having a flexural modulus of from about 250,000 psi to about 310,000 psi (ASTM D790A), with the frame having a brow piece and a pair of symmetric left and right ear pieces extending away from the brow piece at opposite ends of the brow piece, each ear piece terminating at a free end, with the free ends of the brow pieces being spaced apart from one another to define a gap, with the frame having a maximum width such that the ratio of the maximum width to the gap is above 3, and the maximum width of the frame coincides with the distance between bend points of the frame, which bend points represent locations on the frame where the ear pieces bend when flexed and where the ear pieces begin to extend inwardly so as to lie inwardly of the maximum width of the frame.

2. The eyewear frame of claim 1, wherein the gap is less than about 2 inches.

3. The eyewear frame of claim 1, wherein the gap is from about 1.4 inches to about 1.8 inches.

4. The eyewear frame of claim 1, wherein the maximum width is between about 5.6 inches and about 6.2 inches.

5. The eyewear frame of claim 1, wherein the ratio of the maximum width to the gap is between 3 and 5.

6. The eyewear frame of claim 1, wherein the frame is made of plastic having a flexural modulus of 280,000 psi (ASTM D790A).

7. The eyewear frame of claim 6, wherein the plastic is polypropylene.

* * * * *